United States Patent [19]

Weitl et al.

[11] 4,181,654
[45] Jan. 1, 1980

[54] 2,3-DIHYDROXYBENZOIC ACID AMIDS OF TETRAAZAALKANES AND TETAAZA CYCLOALKANES

[75] Inventors: Frederick L. Weitl, Martinez; Kenneth N. Raymond, Berkeley, both of Calif.

[73] Assignee: The United States of America as represented by the United States Department of Energy, Washington, D.C.

[21] Appl. No.: 927,234

[22] Filed: Jul. 24, 1978

[51] Int. Cl.$^2$ .................. C07D 257/02; C07C 103/87
[52] U.S. Cl. .......................... 260/239 BC; 260/559 S; 260/507 R; 252/301.1 W; 252/184; 424/315; 424/244; 424/324
[58] Field of Search .......... 260/239 BC, 559 S, 507 R

[56] References Cited

U.S. PATENT DOCUMENTS

B 403,326  5/1976  Richman ................. 260/239 BC

OTHER PUBLICATIONS

Stetter et al., Berichte, a u, pp. 1410–1416 (1961).
Tait, Biochem. J., vol. 146, pp. 191, 204 (1975).
Ito et al., J.A.C.S., 80, pp. 4645–4648 (1958).
Korth, Arch. Mikrobiol., 70, pp. 297–302 (1970).
Corbin et al., Biochem. 8, pp. 757–762 (1969).

*Primary Examiner*—Alton D. Rollins
*Assistant Examiner*—D. B. Springer
*Attorney, Agent, or Firm*—R. V. Lupo; Roger S. Gaither; Harold M. Dixon

[57] ABSTRACT

A compound of the formula:

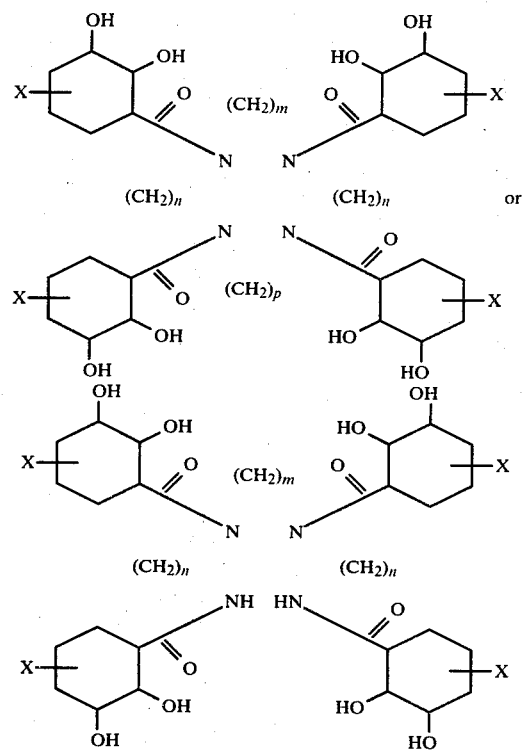

wherein X is hydrogen or a conventional electron-withdrawing group, particularly —SO$_3$H or a salt thereof; n is 2, 3, or 4; m is 2, 3, or 4; and p is 2 or 3. The present compounds are useful as specific sequestering agents for actinide (IV) ions. Also described is a method for the 2,3-dihydroxybenzamidation of azaalkanes.

12 Claims, No Drawings

2,3-DIHYDROXYBENZOIC ACID AMIDES OF TETRAAZAALKANES AND TETAAZA CYCLOALKANES

BACKGROUND OF THE INVENTION

The invention described herein was made at Lawrence Berkeley Laboratory in the course of or under United States Department of Energy Contract No. W-7405-ENG-48 with the University of California.

This invention relates to novel 2,3-dihydroxybenzoic acid amides and to a method for the 2,3-dihydroxybenzamidation of azaalkanes.

Plutonium injected by animals or humans forms stable complexes, so that over a long period of time the body retains some 80% of the original amount ingested, distributed generally between the skeleton and the liver. Because plutonium is such a dangerous carcinogen, the production of specific sequestering agents that enfold it and facilitate its removal is of tremendous importance.

Chemotherapeutic attempts to remove injected plutonium from the tissues of animals have followed along traditional application of such chelating agents as ethylenediaminetetraacetic acid. The results have not been very encouraging since such ligands also complex the trace metal ions essential to the organism and are not extremely strong sequestering agents for the actinides.

Chelating agents for the actinides also have important technological applications. Such agents are useful in the separation of actinide elements, particularly from radioactive wastes generated by fission power reactors. Plutonium is recovered and purified on a commercial scale by extraction in liquid-liquid systems at normal temperature, using organic complexing agents as extractants.

It is known that the 2,3-dihydroxybenzoic (DHB) acid amides of glycine, serine, lysine, threonine, and spermidine are naturally occurring Fe(III) sequestering agents. (References: J. Ito and J. B. Neilands, *J. Am. Chem. Soc.* 80, 4645–4647, 1958; J. L. Corbin and W. A. Bulen, *Biochemistry* 8, 757–762, 1969; H. Korth, *Arch. Mikrobiol.* 70, 297, 1970; and G. H. Tait, *Biochem. J.* 146, 191, 1975). N(DHB)glycine and N(DHB)lysine have been chemically synthesized by the condensation of the O-protected amino acids with DHB acid, mediated by N,N'-dicyclohexylcarbodiimide (see Ito et al, op. cit., and Corbin et al, op. cit.)

SUMMARY OF THE INVENTION

The present invention provides novel specific sequestering agents for actinide (IV) ions, which agents have the following structural formula:

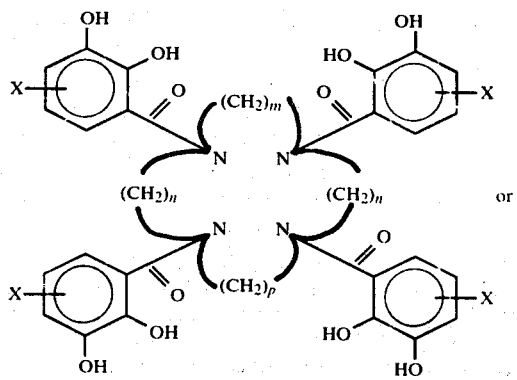

or

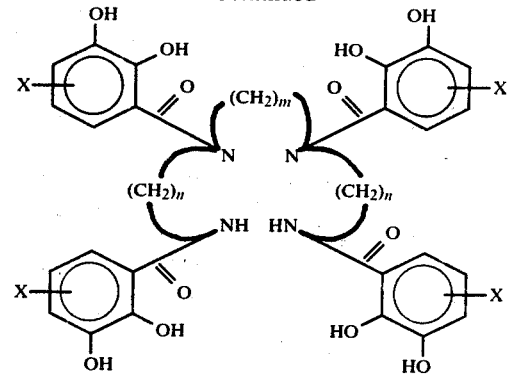

wherein X is hydrogen or a conventional electron-withdrawing group, such as $-SO_3H$ or a salt thereof, $-NO_2$, or the like; n is 2, 3, or 4; m is 2, 3, or 4; and p is 2 or 3. The present compounds form octadentate complexes of actinide (IV) ions, particularly Pu(IV) ions, in which the central metal ion is completely encapsulated by the ligand. The present compounds are useful in the separation of actinide elements, particularly in the separation of plutonium from radioactive wastes. When X is hydrogen, $-SO_3H$ or a pharmaceutically acceptable salt of $-SO_3H$, the compounds are useful as chemotherapeutic agents for removal of ingested plutonium from the tissues of animals.

It is preferred that X be an electron-withdrawing group, particularly $-SO_3H$, since the presence of such a group increases the oxidative stability of the compound and the acidity. Increased acidity is an important consideration for actinide separation processes since, typically, such processes are carried out at relatively low pH. The most preferred compounds for pharmaceutical applications are those wherein X is $-SO_3H$ or a pharmaceutically acceptable salt thereof. Sulfonation increases the solubility by a factor $\approx 10^3$, which permits ready dialysis of the complexed plutonium in the kidney and excretion through the kidney. Sulfonation also increases the oxidative stability and the acidity.

The present invention also provides a general method for the 2,3-dihydroxybenzamidation of azaalkanes in high yield. The term "azaalkanes" is used herein to include azacycloalkanes. In accordance with the present invention, 2,3-dioxomethylenebenzoyl chloride or 2,3-dimethoxybenzoyl chloride is reacted with an azaalkane to produce the corresponding amide. The resulting amide is then demethylated by treatment with boron tribromide ($BBr_3$) or boron trichloride ($BCl_3$) in methylene chloride ($CH_2Cl_2$) solution. Treatment with boron trichloride ($BCl_3$) in $CH_2Cl_2$ solution effects complete removal of the $-CH_2-$ moiety, but not the $CH_3-$ group.

Specifically, the synthetic scheme for the novel compounds of the present invention can be represented as follows:

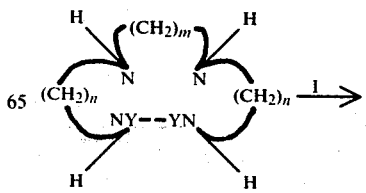

-continued

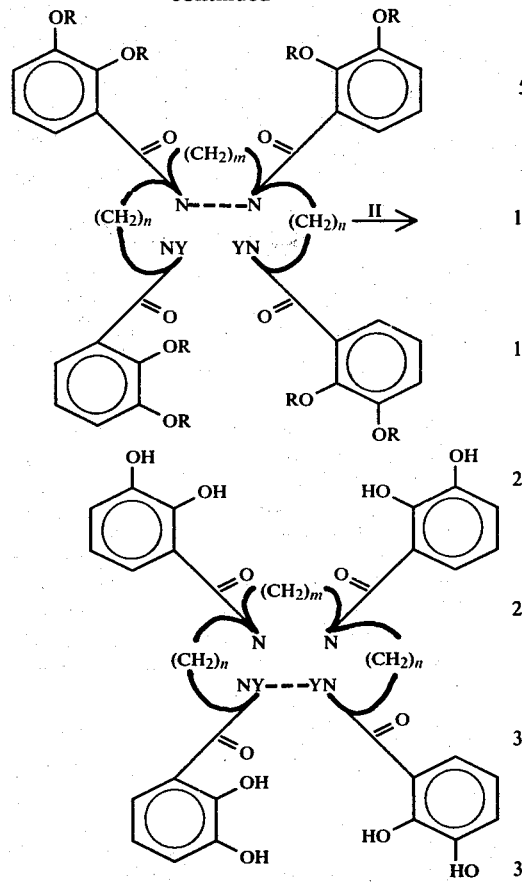

wherein Y represents hydrogen or Y——Y represents —(CH₂)p—; R represents —CH₃ or —CH₂—; and n, m, and p are as previously defined. Reaction I is carried out by reacting the tetraazaalkane with 4 equivalents of 2,3-dioxomethylene- or 2,3-dimethoxybenzoyl chloride in N,N-dimethylacetamide (DMAA) in the presence of 4 equivalents of pyridine for 24–48 hrs at 95°–105° C. or 4-N,N-dimethylaminopyridine for 6–18 hrs at 60°–80°. The DMAA and pyridine function as mediators of the reaction. Demethylation (reaction II) is accomplished in the presence of BBr₃ or BCl₃ in CH₂Cl₂ solution.

Substitution of the catechol rings by conventional electron-withdrawing groups can be accomplished by conventional chemical techniques, either by substitution of the reagent material (2,3-dioxomethylene-or 2,3-dimethoxybenzoyl chloride) or by substitution of the final demethylated amide with the desired substituent.

However, beginning with a pure reagent material such as 5-nitro-2,3-dimethoxybenzoyl chloride will result in a final demethylated amide of 100% isomeric purity. Direct substitution of the final demethylated amide, as in the case of sulfonation, results in an isomeric purity which is dependent upon the regiospecificity of the electrophilic reagents. Sulfonation in this work is regioselective but not regiospecific for the 5-position of the dihydroxybenzamide groups.

It is, therefore, an object of this invention to provide novel specific sequestering agents for actinide (IV), particularly plutonium (IV), ions.

A particular object of this invention is to provide novel compounds suitable for use in the separation of actinide elements, particularly in the separation of plutonium from radioactive wastes.

Another object of this invention is to provide novel compounds suitable for use as chemotherapeutic agents for the removal of ingested plutonium from the tissues of animals.

Yet another object of this invention is to provide a method of sequestering actinide (IV) ions, particularly plutonium (IV) ions.

Still another object of this invention is to provide an improved method for the 2,3-dihydroxybenzamidation of azaalkanes, particularly tetraazaalkanes.

Other objects and advantages will become apparent from the following detailed description.

DETAILED DESCRIPTION OF PREFERRED EMBODIMENTS

A tabular summary of compounds illustrative of the present invention is given in Table I. Detailed synthesis procedures for selected compounds follows Table 1.

Table 1.
TETRA(2,3-DIHYDROXYBENZOYL)TETRAAZAALKANES

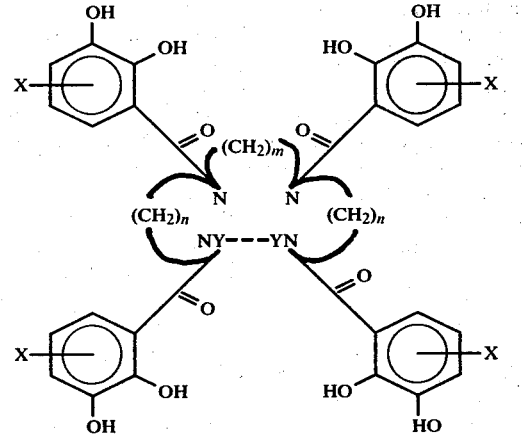

| a. Y——Y is —(CH₂)p— | | | | |
|---|---|---|---|---|
| No. | n | m | p | X |
| 1 | 2 | 3 | 3 | H |
| 2 | 2 | 3 | 3 | —NO₂ |
| 3 | 3 | 3 | 3 | H |
| 4 | 3 | 3 | 3 | —SO₃Na |
| 5 | 3 | 3 | 2 | H |
| 6 | 3 | 3 | 2 | —SO₃K |

| b. Y = H | | | |
|---|---|---|---|
| No. | n | m | X |
| 7 | 4 | 4 | H |
| 8 | 4 | 4 | —SO₃Na |
| 9 | 2 | 3 | H |
| 10 | 2 | 3 | —SO₃K |

Compound 1.
1,4,8,11-N,N',N'',N'''-Tetra(2,3-dihydroxybenzoyl)tetraazacyclotetradecane Preparation of 1,4,8,11-tetra(2,3-dioxomethylenebenzoyl)tetraazacyclotetradecane (precursor 1)

Refluxing 3.4 q(20.5 mmol) of 2,3-dioxomethylenebenzoic acid in 20 ml SOCl₂ under a Drierite tube for several hours gave a solution, which was evaporated to residue. Coevaporation with benzene (3×30 ml) removed traces of excess SOCl₂ to give the corresponding benzene-soluble acid chloride to which 30 ml of DMAA were added followed by 1.0 g (5.0 mmol) 1,4,8,11-tetraazacyclotetradecane and 1.6 g (20.2 mmol) pyridine. The resulting mixture was heated at 95° C. for 72 hours in a stoppered, 100 ml round bottom flask immersed in an oil bath. The evaporation of the DMAA gave a residue which was partitioned between $CHCl_3$ and $H_2O$. The $CHCl_3$ layer was washed several times with $H_2O$ then concentrated and placed upon a silica gel column (15"×¾" O.D.) prepared in $CCl_4$. The product (precursor 1), 3.65 g (92%), was obtained after elution with 4% EtOH in $CHCl_3$ solution and crystallized from $CHCl_3$: tlc, $R_f$ 0.61; H-nmr (TFA) δ 2.0–2.8 (broad m, 4H, >N—$CH_2CH_2CH_2$—), 3.3–4.5 (broad m, 16H, >N—$CH_2$—$CH_2$—), 5.90 (broad s, 4H, —O—$CH_2$—O—), 6.10 (broad s, 4H, —O—$CH_2$—O—), 7.03 (broad s, 12H, aromatic); ir, 1615 and 1445 (>N—CO—), 1050, 925 and 745 (—$OCH_2O$—) $cm^{-1}$.

Anal. Calcd. for $C_{42}H_{40}N_4O_{12}$: C, 63.63; H, 5.09; N, 7.07. Found: C, 63.48; H, 5.17; N, 7.04.

Preparation of 1,4,8,11-N',N'',N''',N''''-tetra(2,3-dimethoxybenzoyl)tetraazacyclotetradecane (precursor 2)

To 4.55 g (25 mmol) 2,3-dimethoxybenzoic acid was added 15 ml $SOCl_2$ and the slurry was stirred at room temperature for 2 hours under a Drierite tube. The resulting solution was evaporated to a residue, then coevaporated with benzene (3×30 ml) to remove traces of $SOCl_2$. To the resulting benzenesoluble acid chloride was added:

1.0 g (5.0 mmol) 1,4,8,11-tetraazacyclotetradecane, 40 ml DMAA, 2.0 g (25 mmol) pyridine. Using the same procedure as for precursor 1, the product (precursor 2), 4.6 g (87%) was isolated after elution from silica gel with $CHCl_3$ then precipitated from $CHCl_3$ with $Et_2O$: tlc, $R_f$ 0.55; H-nmr ($CDCl_3$) 1.8–2.4 (broad m, 4H, >N—$CH_2CH_2CH_2$—), 2.8–3.8 (broad m. 16H, >N—$CH_2CH_2$—), 3.88 (broad s, 24H, —$OCH_3$), 6.7–7.3 (broad m, 12H, aromatic); ir, 1635, 1475, 1425 (>N—CO—), 1310, 1265, 1230, 1045, 1000, 795, 750 (—$OCH_3$) $cm^{-1}$.

Anal. Calcd. for $C_{46}H_{56}N_4O_{12}$: C, 64.47; H, 6.59, N, 6.54. Found: C, 62.97; H, 6.57; N, 6.20.

Method A

To a solution of 0.79 g (1.0 mmol) precursor 1 in 15 ml $CH_2Cl_2$ under Argon atmosphere, vigorously stirred with a magnetic bar and immersed in an ice bath, was added via syringe and septum 30 ml 1 M $BCl_3/CH_2Cl_2$ solution. An immediate precipitate formed and was stirred overnight, while the ice bath was allowed to warm up to room temperature. Next the addition of 20 ml $H_2O$ via syringe (4×5 ml aliquots added over 20 minutes) quenched the excess $BCl_3$ and the resulting mixture was stirred an additional 1.5 hours at room temperature. Evaporation to residue followed by coevaporation with MeOH (3×50 ml) removed all boron as methylborate. The white residue was then dried in a vacuum oven at 95° C. overnight to obtain 0.75 g (~100%) compound 1: H-nmr ($D^6MSO$—$D_2O$) showed the complete absence of the —$OCH_2O$— (δ~6.0) moiety and the nmr sample turned deep blue when treated with aqueous $FeCl_3$.

Anal. Calcd. for $C_{38}H_{40}N_4O_{12}\cdot2.5H_2O$: C, 57.79; H, 5.74; N, 7.09; O, 29.38. Found: C, 57.86; H, 5.92, N, 6.92; O, 29.50.

Method B

To a solution of 1.0 g (1.2 mmol) precursor 2 in 20 ml $CH_2Cl_2$ under Argon atmosphere and cooled by an ice bath was added via syringe and septum 3 ml (7.8 g, 31 mmol) neat $BBr_3$. The resulting slurry was stirred overnight as the ice bath was allowed to warm up to room temperature. Workup in the same way as for Method A gave 0.9 g (18 100%) compound 1: H-nmr ($D^6MSO$—$D_2O$) showed the complete absence of the —$OCH_3$ (δ≈3.9) moiety and the product was identical to that produced in Method A.

Preparation of 1,4,8,11-tetra(2,3-dimethoxy-5-nitrobenzoyl)-tetraazacyclotetradecane (precursor 3)

Refluxing 4.8 g (21 mmol) of 5-nitro-2,3-dimethoxybenzoic acid in 20 ml $SOCl_2$ under a Drierite tube for 5 hr gave a solution which was coevaporated with benzene to a dry crystalline solid. To this crude acid chloride was added 25 ml DMAA followed by 1.0 g (5.0 mmol) 1,4,8,11-tetraazacyclotetradecane and 1.7 g (21 mmol) $NaHCO_3$ powder. The reaction mixture was heated at 95° under argon for 17 hr while vigorously stirred. Evaporation in vacuo of the DMAA followed by $CHCl_3/H_2O$ partitioning of the products then an aqueous NaOH wash of the organic layer gave the crude product - $CHCl_3$ solution. The latter was eluted from a basic (CAMAG) alumina column with 5% EtOH in $CHCl_3$. Thus was obtained yellow-tan solid which recrystallized from hot EtOH to give precursor 3, 1.7 g (33%): m.p. 232°–5°; H-nmr ($CDCl_3$) δ1.7–2.5 (broad m, 4H, >N—$CH_2$—$CH_2$—$CH_2$), 2.8–3.8 (broad m, 16H, >N—$CH_2$—$CH_2$—), 4.0 (s, 24H, —$OCH_3$), 7.4–8.0 (broad m, 8H, aromatic); IR (KBr) 1640 (>N—CO—), 1525 (—$NO_2$), 1340 (—$NO_2$), 1095, 1050 (—$OCH_3$), 990 (—$OCH_3$), 740 $cm^{-1}$.

Anal. Calcd. for $C_{46}H_{52}N_8O_{20}$: C, 53.28; H, 5.05; N, 10.81. Found: C, 52.22; H, 4.96; N, 10.58.

Compound 2

Using method B, precursor 3 (1.0 g, 1.0 mmol) dissolved in $CH_2Cl_2$ (25 ml) was added dropwise (15 min) via an addition funnel to an ice bath cooled, vigorously stirred solution of $BBr_3$ (2 ml, 21 mmol) in $CH_2Cl_2$ solution (25 ml). The ice bath was allowed to warm up to room temperature as the reaction slurry was stirred overnight. Cautious addition of $H_2O$ (20 ml) was followed by an additional 2 hrs stirring to hydrolyze all boron compounds. Crude product was collected by filtration and washed well with $H_2O$. The pink-tan solid was dissolved in MeOH and precipitated by the addition of $Et_2O$. Drying at 115° (5–10 microns) overnight gave the demethylated product, compound 2 (0.88 mmol, 88%) as hygroscopic powder which analyzed with two waters of crystallization: m.p. 230°–40° dec., H-nmr ($D^6MSO$—$D_2O$) showed complete absence of —$OCH_3$ (δ≈4.0 moiety); purity also established by pH-titration giving $pKa_1$ 5.59 (4 protons) and $pKa_2$ 11.8 (4 protons) for the 4 constituent catechol groups.

Anal. Calcd. for $C_{38}H_{36}N_8O_{20}$ 2 $H_2O$: c, 47.50; H, 4.20; N, 11.66. Found: C, 47.52; H, 4.23; N, 9.74.

Compound 3.
1,5,9,13-N,N',N'',N'''-Tetra(2,3-dihydroxybenzoyl)tetraazacyclohexadecane Preparation of
1,5,9,13-N,N',N'',N'''-tetra(2,3-dioxomethylenebenzoyl)tetraazacyclohexadecane (precursor 4)

Using the same procedure as for precursor 1, the following were heated together at 95° C. for 88 hours: 2,3-dioxomethylene-benzoylchloride [prepared from 3.5 g (21.0 mmol) of the benzoic acid]; 1.10 g (5.0 mmol) of 1,5,9,13-tetraazacyclohexadecane; 1.7 g (21.5 mmol) of pyridine; 30 ml DMAA. Workup as for precursor 1 resulted in precursor 4, 2.6 g (63%) which was crystallized from $CH_2Cl_2$: tlc, $R_f$ 0.58; H-nmr ($CDCl_3$) 1.6–2.4 (broad s, 8H, >N—$CH_2\underline{CH_2}$—$CH_2$), 2.9–3.8 (broad s, 16H, >N—$\underline{CH_2}CH_2$—), 5.93 (s, 8H, —O$\underline{CH_2}$O—), 6.80 (s, 12H, aromatic); ir, 1625 and 1595 (>N—CO—). 1445, 1250, 1055, 1030, 925, 745 (—O$\underline{CH_2}$O) cm$^{-1}$.

Anal. Calcd. for $C_{44}H_{44}N_4O_{12}$: C, 64.38; H, 5.40; N, 6.83. Found: C, 64.11; H, 5.31; N, 6.70.

Using Method A the following reagents were combined: 0.82 g (1.0 mmol) precursor 4, 30 ml 1 M $BCl_3/CH_2Cl_2$ solution and 15 ml $CH_2Cl_2$. Workup gave 0.8 g (~100%) of compound 3: H-nmr ($D^6MSO$—$D_2O$) showed the complete absence of the —O$CH_2$O—($\delta$>6.0) moiety. A sample dried at 100° C. in vacuo gave the correct elemental analysis for compound 3.2$H_2O$.

Anal. Calcd. for $C_{40}H_{44}N_4O_{12}.2H_2O$: C, 59.40; H, 5.98; N, 6.93. Found: C, 59.09; H, 5.70; N, 6.82.

Compound 4.
1,5,9,13-N,N',N'',N'''-Tetra(2,3-dihydroxybenzoyl)-tetraazacyclohexadecane sodium sulfonate

Method C

Compound 3 (1.0 g, 1.2 mmol) was dissolved in 30% fuming $H_2SO_4$ (10 ml) and stirred overnight in a stoppered flask immersed in a room temperature water bath. The reaction solution was then poured onto ice resulting in a clear aqueous ($\approx$100 ml) solution. Careful addition of solid NaOH, with water bath cooling, gave a pH 4 solution. Addition of 2–3 volumes of MeOH provided a copious white, inorganic precipitate. This was removed by filtration and discarded. The product solution was evaporated to dryness, the solid redissolved in MeOH and filtered. Addition of 2.3 volumes of $Et_2O$ to the clear solution gave a hygroscopic white solid, this was collected by filtration and dried at 115° (5–10 microns) overnight to obtain 1.4 g (1.1 mmol, 89%) compound 4.5 $H_2O$: IR (KBr) 2800–3700 s, 1610 s (>N—CO), 1485, 1410 m, 1150–1250 s (—$SO_3^-$), 1100, 1045 s (—$SO_3^-$), 615 (—$SO_3^-$).

Anal. Calcd. for $C_{40}H_{40}N_4O_{24}S_4Na_4.5\ H_2O$: C, 37.80; H, 3.96; N, 4.41; S, 10.09; Na, 7.23. Found: C, 37.52; H, 3.94; N, 4.39; S, 9.74; Na, 8.60.

Method D

Compound 3 (1.0 g, 1.2 mmol) was dissolved in 98% $H_2SO_4$ (5 ml), then $SOCl_2$ (5 ml, 55 mmol) was added dropwise over a period of 1 hr with vigorous stirring. The reactants were protected from the atmosphere with a Drierite tube. After stirring overnight, the reaction mixture was poured onto ice. Workup as in method C gave white solid, 1.49 g (1.0 mmol, 85%) which analyzed as compound 4.3 $NaCl.H_2O$: IR (KBr) identical to that recorded in method A; purity also established by pH-titration giving $pKa_1$ 8.12 (4 protons) and $pKa_2$ 12.0 (4 protons) for the four constitutent catechol groups.

Anal. Calcd. for $C_{40}H_{40}N_4O_{24}S_4Na_4.3\ NaCl.H_2O$: C, 34.96; H, 3.08; N, 4.08; S, 9.33; Cl, 7.74; Na, 11.71. Found: C 34.93; H, 3.66; N, 4.12; S, 8.18; Cl, 7.77; Na, 12.5.

1,4,8,12-N, N',N'',N'''-tetra(2,3-dihydroxybenzoyl)-tetraazacyclopentadecane (compound 5) and its potassium sulfonate (compound 6) were prepared by procedures similar to those described above.

Compound 8.
1,6,11,16-N,N',N'',N'''-Tetra(2,3-dihydroxybenzoyl)tetraazahexadecane potassium sulfonate Preparation of
1,6,11,16-N,N',N'',N'''-tetra(2,3-dimethoxybenzoyl)tetraazahexadecane (precursor 5)

Using nearly the same procedure as for precursor 2, the following were heated together at 80° C. for 16 hours: 2,3-dimethoxybenzoyl chloride [prepared from 6.4 g (35 mmol) of the benzoic acid]; 2.0 g (8.7 mmol) of 1,6,11,16-tetraazahexadecane; 4.3 g (35 mmol) 4-N,N-dimethylaminopyridine; 35 ml DMAA. The resulting reaction mixture was evaporated to residue in vacuo and the products partitioned between $H_2O$ and $CHCl_3$. The $CHCl_3$ layer was washed well with dilute aqueous HCl and then dilute aqueous NaOH before drying with $MgSO_4$ and eluting from a silica gel column as in the preparation of precursor 1. Thus was obtained product (precursor 5), 6.6 g (86%) as glassy solid: IR (KBr) 3400 m (—NHCO—), 2940 (CH), 1655 and 1635 s (>N—CO) cm$^{-1}$.

Anal. Calcd. for $C_{48}H_{62}N_4O_{12}$: C, 64.99; H, 7.05; N, 6.32. Found: C, 64.18; H, 6.82; N, 6.23.

1,6,11,16-N,N',N'',N'''-tetra(2,3-dihydroxybenzoyl)-tetraazahexadecane (compound 7) was prepared from precursor 5 using Method B as in the preparation of compound 1.

Using precisely the same Method D, compound 7 was converted to compound 8. Thus was obtained hygroscopic white solid, 1.4 g (90%); IR (KBr) 2800–3700 s, 1600 s (>N—CO—), 1475, 1425 m, 1150–1300 s (—$SO_3^-$), 1100, 1045 s (—$SO_3^-$), 620 (—$SO_3^-$); purity also established by pH-titration giving $pKa_1$ 7.49 (4 protons) and $pKa_2$ 12.1 (4 protons) for the four constituent catechol groups.

Anal. Calcd. for $C_{40}H_{42}N_4O_{24}S_4Na_4.\frac{1}{2}NaCl.\frac{1}{4}\ Na_2SO_4.3\ H_2O$: C, 36.91; H, 3.72; N, 4.31; S, 10.47; Cl, 1.36; Na, 8.83. Found: C, 36.91; H, 3.82; N, 4.37; S, 10.82; Cl, 1.04; Na, 8.83.

1,4,8,11-N,N',N'',N'''-tetra(2,3-dihydroxybenzoyl)-tetraazaundecane (compound 9) and its potassium sulfonate (compound 10) were prepared from the corresponding tetraazaundecane by the same procedures as for compound 8.

By qualitative observations, it was found that Pu(IV) dissolved in the presence of compound 1 even at high pH. Since the $K_{sp}$ for $Pu(OH)_4$ is approximately $10^{-52}$, this indicates a very high formation constant for the Pu(IV) complex of compound 1.

The actinide-ion sequestering activity of the compounds of the present invention was also demonstrated by animal studies. Specifically, animal studies were carried out with compounds 2, 3, 4, and 10. (NOTE: compound 2, the nitro derivative, is not suitable as a chemotherapeutic agent since it is toxic to animals. The animal studies serve to demonstrate the actinide-ion sequestering activity of the compound. Compound 2 is suitable for use in the separation of actinide elements.) The results of the animal studies are summarized below.

Compound 2.
1,4,8,11-N,N',N'',N'''-Tetra(2,3-dihydroxy-4-nitrobenzoyl)tetraazacyclotetradecane.

Distribution of $^{238}$Pu-Citrate in Mouse Tissues

| | Control 2[b] | | Compound 2[b] | |
|---|---|---|---|---|
| # of animals per Group | 5 | | 5 | |
| Age of animals | 74 weeks | | 74 weeks | |
| # of Days After Pu Injection-Killed | 2 | | 2 | |
| | $\bar{x}$ | $\sigma$ | $\bar{x}$ | $\sigma$ |
| Liver | 38.2 | ± 6.3 | 36.6 | ± 8.2 |
| Skel | 35.8 | ± 4.6 | 7.9 | ± 0.8 |
| Soft Tis | 8.6 | ± 1.0 | 14.8 | ± 1.5 |
| Skin | 4.1 | ± 0.5 | 11.2 | ± 2.5 |
| G.I. | 10.1 | ± 1.7 | 16.3 | ± 3.7 |
| Kidney | 1.3 | ± 0.8 | 6.0 | ± 1.5 |
| Urine | 0.9 | — | 1.8 | — |
| Feces | 0.9 | — | 5.4 | — |
| Total | 99.9 | — | 100 | — |

[b]Animals injected I.P. (Intraperitoneum)

Compound 3.
1,5,9,13-N,N',N'',N'''-Tetra(2,3-dihydroxybenzoyl)tetraazacyclohexadecane.

Distribution of $^{238}$Pu-citrate in Mouse Tissues

| | Controls 3[a] | | Compound 3[a] | |
|---|---|---|---|---|
| # of Animals per Group | 5 | | 10 | |
| Age of Animals | 68 weeks | | 68 weeks | |
| # of days after Pu Injection-Killed | 2 | | 2 | |
| | $\bar{x}$ | $\sigma$ | $\bar{x}$ | $\sigma$ |
| Liver | 40.0 | ±13.7 | 23.3 | ±5.7 |
| Skel / Sof Tis | 44.1 | ±11.4 | 20.3 | ±5.6 |
| Skin | — | — | — | — |
| G.I. | 7.4 | — | 4.4 | — |
| Kidney | 3.4 | — | 42.1 | — |
| Urine / Feces | 4.9 | — | 11.5 | — |
| Total | 99.8 | — | 101.6 | — |

[a]Animals injected I.M. (Intramuscular)

Compound 4.
1,5,9,13-N,N',N'',N'''-Tetra(2,3-dihydroxybenzoyl)tetraazacyclohexadecane sodium sulfonate.

Distribution of $^{238}$Pu-citrate in Mouse Tissues

| | Controls 4[b] | | Compound 4[b] | |
|---|---|---|---|---|
| # of Animals per Group | 5 | | 5 | |
| Age of Animals | 13.5 weeks | | 13.5 weeks | |
| # of Days after Pu injection killed | 1 | | 1 | |
| | $\bar{x}$ | $\sigma$ | $\bar{x}$ | $\sigma$ |
| Liver | 46.3 | ± 8.2 | 24.8 | ± 3.7 |
| Skel | 33.8 | ± 8.8 | 15.7 | ± 3.1 |
| Soft Tis | 3.6 | ± 0.7 | 6.4 | ± 2.2 |
| Skin | 1.8 | ± 0.5 | 4.1 | ± 0.7 |
| G.I. | 7.9 | ± 1.6 | 8.2 | ± 0.6 |
| Kidney | 1.2 | ± 0.3 | 3.9 | ± 0.5 |
| Urine | 2.3 | — | 33.8 | — |

Compound 4. -continued
1,5,9,13-N,N',N'',N'''-Tetra(2,3-dihydroxybenzoyl)tetraazacyclohexadecane sodium sulfonate.

| | | | | |
|---|---|---|---|---|
| Feces | 2.8 | — | 3.1 | — |
| Total | 99.7 | — | 100 | — |

[b]Animals injected I.P.

Compound 10.
1,4,8,11-N,N',N'',N'''-Tetra(2,3-dihydroxybenzoyl)tetraazaundecane potassium sulfonate Distribution of $^{238}$Pu-citrate in Mouse Tissues

| | Controls 10[a] | | Compound 10[a] | |
|---|---|---|---|---|
| # of Animals per group | 5 | | 5 | |
| Age of animals | 18 weeks | | 18 weeks | |
| # days after Pu injection killed | 1 | | 1 | |
| | $\bar{x}$ | $\sigma$ | $\bar{x}$ | $\sigma$ |
| Liver | 49.8 | ± 10.7 | 28.8 | ± 2.4 |
| Skel | 33.0 | ± 5.7 | 12.1 | ± 1.0 |
| Soft Tis | 4.8 | ± 0.8 | 7.1 | ± 1.0 |
| Skin | 4.8 | ± 0.8 | 5.7 | ± 1.0 |
| G.I. | 10.0 | ± 0.6 | 10.2 | ± 1.0 |
| Kidney | 1.6 | ± 0.3 | 4.8 | ± 0.3 |
| Urine | 1.0 | — | 29.2 | — |
| Feces | 1.1 | — | 2.2 | — |
| Total | 101.3 | — | 101.1 | — |

[a]Animals injected I.M.

It is evident from the results of the animal studies that the compounds of the present invention markedly alter the distribution of Pu ion in animal tissues, concentrating the Pu ion in the kidney, from which it may be excreted, instead of the liver or skeleton. The sulfonated compounds are particularly effective for removal of ingested Pu ion; the resulting Pu complex is readily dialyzed in the kidney and excreted in the urine. Toxicity studies with compound 3 and with its sulfonated derivative indicate that these compounds are substantially acutely non-toxic. For those compounds of the present invention which are useful as chemotherapeutic agents, administration may be accomplished by intravenous injection of a solution of the agent in a pharmaceutically acceptable carrier.

It is reiterated that all of the compounds of the present invention may be used in the separation of actinide elements by extraction through complex formation, using techniques well established in the art.

Although the invention has been hereinbefore described with reference to specific examples, various modifications and changes will be apparent to those skilled in the art without departing from the true spirit of the invention.

What we claim is:

1. A compound of the formula:

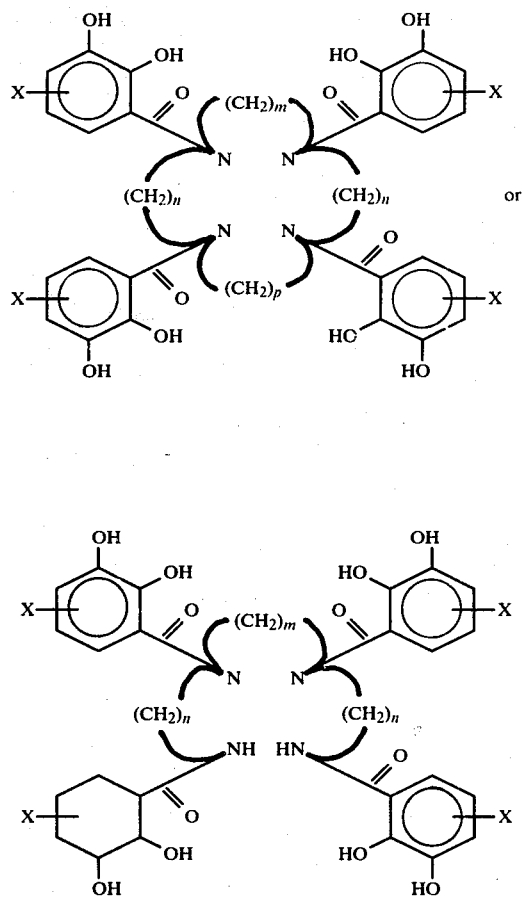

wherein X is hydrogen, —SO₃H or a salt thereof, or —NO₂; n is 2, 3, or 4; m is 2, 3, or 4; and p is 2 or 3.

2. A compound as in claim 1 wherein the formula is

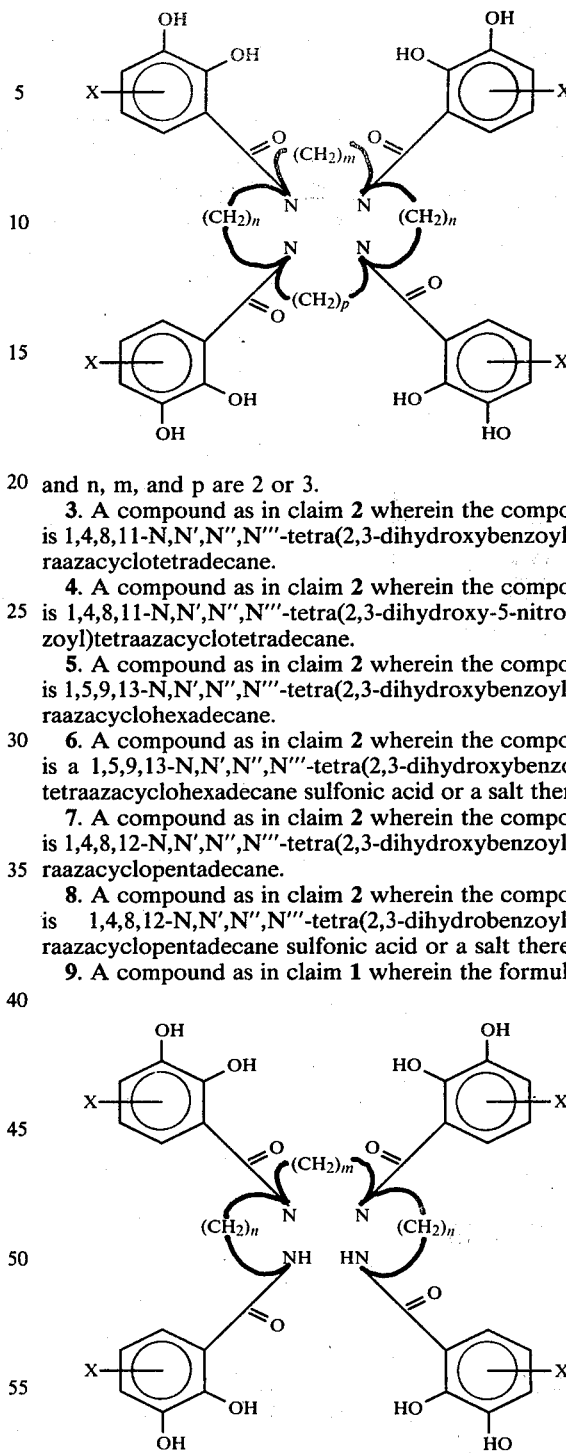

and n, m, and p are 2 or 3.

3. A compound as in claim 2 wherein the compound is 1,4,8,11-N,N',N'',N'''-tetra(2,3-dihydroxybenzoyl)tetraazacyclotetradecane.

4. A compound as in claim 2 wherein the compound is 1,4,8,11-N,N',N'',N'''-tetra(2,3-dihydroxy-5-nitrobenzoyl)tetraazacyclotetradecane.

5. A compound as in claim 2 wherein the compound is 1,5,9,13-N,N',N'',N'''-tetra(2,3-dihydroxybenzoyl)tetraazacyclohexadecane.

6. A compound as in claim 2 wherein the compound is a 1,5,9,13-N,N',N'',N'''-tetra(2,3-dihydroxybenzoyl)-tetraazacyclohexadecane sulfonic acid or a salt thereof.

7. A compound as in claim 2 wherein the compound is 1,4,8,12-N,N',N'',N'''-tetra(2,3-dihydroxybenzoyl)tetraazacyclopentadecane.

8. A compound as in claim 2 wherein the compound is 1,4,8,12-N,N',N'',N'''-tetra(2,3-dihydrobenzoyl)tetraazacyclopentadecane sulfonic acid or a salt thereof.

9. A compound as in claim 1 wherein the formula is

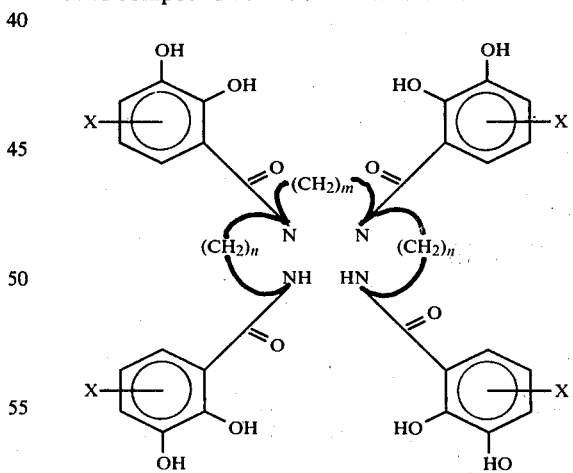

10. A compound as in claim 9 wherein the compound is 1,4,8,11-N,N',N'',N'''-tetra(2,3-dihydroxybenzoyl)tetraazaundecane.

11. A compound as in claim 9 wherein the compound is 1,4,8,11-N,N',N'',N'''-tetra(2,3-dihydroxybenzoyl)tetraazaundecane sulfonic acid or a salt thereof.

12. A compound as in claim 9 wherein the compound is 1,6,11,16-N,N',N'',N'''-tetra(2,3-dihydroxybenzoyl)-tetraazahexadecane.

* * * * *